United States Patent

Kåhre

[11] Patent Number: 5,742,382
[45] Date of Patent: Apr. 21, 1998

[54] REFRACTOMETER

[75] Inventor: Jan Kåhre, Helsinki, Finland

[73] Assignee: Janeksko Oy, Vantaa, Finland

[21] Appl. No.: 589,568

[22] Filed: Jan. 22, 1996

Related U.S. Application Data

[63] Continuation of Ser. No. 296,676, Aug. 26, 1994, abandoned.

[30] Foreign Application Priority Data

Sep. 7, 1993 [FI] Finland .................... 933907

[51] Int. Cl.$^6$ .................................................. G01N 21/41
[52] U.S. Cl. ................................................................ 356/136
[58] Field of Search ................................. 356/128–137; 250/573, 227.25, 577

[56] References Cited

U.S. PATENT DOCUMENTS

| | | | |
|---|---|---|---|
| 4,320,291 | 3/1982 | Uramoto | 356/136 |
| 4,639,594 | 1/1987 | Schoch et al. | 356/133 |
| 4,640,616 | 2/1987 | Michalik | 356/136 |
| 4,699,511 | 10/1987 | Seaver | 356/135 |
| 4,699,516 | 10/1987 | Bartz et al. | 356/136 |
| 4,844,608 | 7/1989 | Smith | 356/136 |
| 4,998,022 | 3/1991 | Tregay | 356/136 |

FOREIGN PATENT DOCUMENTS

| | | | |
|---|---|---|---|
| 0184911 | 6/1986 | European Pat. Off. | |
| 0283426 | 9/1988 | European Pat. Off. | |
| 0359167 | 3/1990 | European Pat. Off. | 356/135 |
| 0197633 | 8/1989 | Japan | 356/133 |
| 1320449 | 12/1989 | Japan | 356/135 |

Primary Examiner—Hao Q. Pham
Attorney, Agent, or Firm—Fitch, Even, Tabin & Flannery

[57] ABSTRACT

A refractometer, comprising a frame structure, in which are arranged a light source, an optical window and a light sensitive detector, whereby the optical window is arranged to be positioned into contact with a solution to be measured and a beam of rays from the light source is arranged to be directed to an interface between the optical window and the solution, whereby part of the ray beam reflects back from the solution and part of it is absorbed partially into the solution and an image is created, in which the location of a borderline between a light and a dark area depends on the critical angle of total reflection, this angle being a function of the concentration of the solution, and whereby an information of the location of the borderline is arranged to be transformed into an electrical form by the light sensitive detector. To provide a ray beam having an even angular distribution, a fibre optic clad rod is arranged between the light source and the optical window, which clad rod consists of one optical fibre, through which the ray beam is arranged to pass to the optical window.

7 Claims, 1 Drawing Sheet

REFRACTOMETER

This application is a continuation of application Ser. No. 08/296,676 filed Aug. 26, 1994 now abandoned.

BACKGROUND OF THE INVENTION

The invention relates to a refractometer, comprising a frame structure, in which are arranged a light source, an optical window and a light sensitive detector, whereby the optical window is arranged to be positioned into contact with a solution to be measured and a beam of rays from the light source is arranged to be directed to an interface between the optical window and the solution, whereby part of the ray beam reflects back from the solution and part of it is absorbed partially into the solution and an image is created, in which the location of a borderline between a light and a dark area depends on the critical angle of total reflection, this angle being a function of the concentration of the solution, whereby an information of the location of the borderline is arranged to be transformed into an electrical form by means of the light sensitive detector and whereby a fibre optics is arranged between the light source and the optical window, the fibre optics comprising at least one optical fibre, through which the ray beam is arranged to pass to the optical window.

The operating principle of the refractometer is known since over a hundred years already. At present, refractometers are used rather much in a plurality of different fields. As examples of the fields where refractometers are used may be mentioned food industry, wood-processing industry, chemical industry and research of different kind in general.

An essential feature of refractometer measurement consists of analyzing an image created by light reflection. The purpose of such an image analysis is to find the location of the critical angle of total reflection, i.e. the borderline at which the light area turns into the dark area.

In prior art applications, several different principles of finding the critical angle of total reflection have been used. As an example of such principles may be mentioned an idea, according to which the brightness of the light area is constant at different critical angles. Then the amount of light obtained from the whole image area corresponds to the share of the light area in the whole area. Many commercial instruments use this principle. However, a drawback of the principle is its sensitivity to variations of light source and optical path.

As another known principle may be mentioned a solution, in which an image reflected from the optical window of the refractometer is looked at with a row camera. A row camera comprises many light detectors, e.g. 256, integrated in a row for the same microcircuit. The amounts of light measured by the detectors can be read alternately in the camera. The location of the critical angle of total reflection can be determined by counting the number of the detectors exceeding a threshold value. Such a principle is used for instance in refractometers PR-01-B, PR-01-E and PR-01-S manufactured and sold by K-Patents Oy.

The devices described above operate well in principle, but problems arise in practice, caused by uneven angular distribution of the beam of light rays directed to the optical window. For the accuracy of the final result, it is essential that the angular distribution of the ray beam is as even as possible. In previous solutions, the angular distribution of the ray beam has not been as even as could be desired, which has sometimes led to relatively cumbersome implementations in order to make the angular distribution satisfactorily even.

SUMMARY OF THE INVENTION

The object of the invention is to provide a solution, by means of which the drawbacks of the previously known technique can be eliminated. This has been achieved by means of the refractometer according to the invention, which is characterized in that the fibre optics consists of one clad rod having a predetermined diameter.

A primary advantage of the invention is that a very even angular distribution of a ray beam can be provided by means of the invention in a simple manner, through which the accuracy of the measurement is improved in comparison to the previous solutions. Even angular distribution means here that all angles of the ray beam include an identical amount of light. An advantage is also the simplicity of the invention, which makes it preferable to start using the invention. Still an advantage is that no focusing optics is needed between the light source and the fibre optics, but the light can be led directly to the clad rod formed by the fibre optics.

BRIEF DESCRIPTION OF THE DRAWINGS

In the following, the invention will be explained in greater detail by means of a preferred embodiment shown in the attached drawing, whereby.

DESCRIPTIONS

Figures 1, 2, 3:
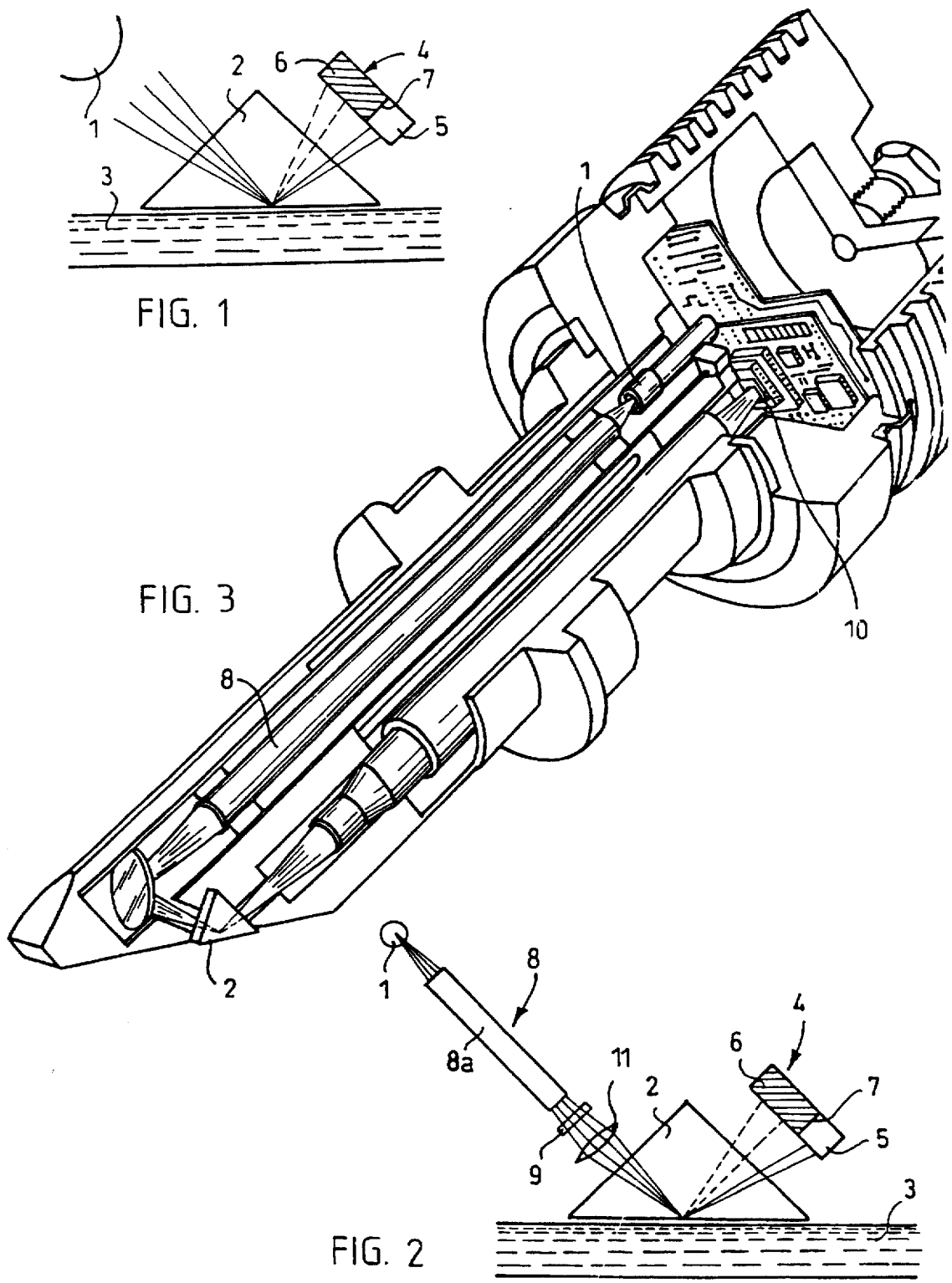
FIG. 1 is a general view of the operating principle of a refractometer.
FIG. 2 illustrates the basic principle of the invention essentially adapted to the situation of FIG. 1
FIG. 3 shows an example of a refractometer, to which the solution according to the invention is applied.

A refractometer used in a process, e.g. in wood-processing, for measuring the concentration of a process solution is called a process refractometer. A process refractometer is located in a process in such a way that the optical window of a measuring head of the refractometer, which window is a prism, for instance, is in contact with the process solution. The process refractometer measures the refractive index of the process solution by means of the total reflection created at the interface between the prism of the measuring head and the process solution. FIG. 1 shows the above measuring principle in general.

A beam of rays from a light source 1 is directed to the interface between a prism 2 and a process solution 3. Part of the ray beam is reflected back from the solution entirely, part of it is absorbed partially into the solution. The reflection of the ray beam creates an image 4, in which the location of a borderline 7 between a light area 5 and a dark area 6 depends on the critical angle of total reflection and so on refractive index. The concentration of the process solution is found out by determining the location of the borderline 7 between the light area 5 and the dark area 6 in the image 4. The location of the borderline 7 can be determined by means of light detectors arranged in a row. The number of light detectors used for the measurement is high, the process refractometer PR-01-S manufactured and sold by K-Patents Oy has for instance 256 light detectors integrated for the same microcircuit. The detector formed by the light detectors transforms the image 4 point by point into an electric signal. A certain signal is received from the light detectors of the light area and a certain signal from the light detectors of the dark area.

The above measuring principle and the operation of the refractometer in general consist of a technique fully known by one skilled in the art, and therefore, they are not described in more detail in this connection.

FIG. 2 illustrates the basic principle of the refractometer according to the invention, essentially adapted to the embodiment of FIG. 1. FIG. 2 uses the same reference numerals as FIG. 1 for identical points.

According to the essential idea of the invention, a fibre optics 8 is arranged between the light source 1 and the optical window 2, through which fibre optics a beam of rays is arranged to pass to the optical window 2. The fibre optics 8 consists of one optical clad rod 8a. The thickness of the clad rod is fitted to the light source and can be a few millimetres, for instance. An example of a typical diameter could be a range essentially within 1 to 2 mm. The thickness of the clad rod is selected so as to make a sufficient amount of light pass through it. The embodiment utilizing a clad rod is based on the fact that the clad rod fitted to the light source collects the conical ray beam coming from the light source and cuts sharply away wide angles and mixes and homogenizes the light. It is essential that only the part of the light flows to the optical window that reflects within the fibre optics 8 from one wall to another or passes directly through the fibre. When passing through the fibre optics 8, the majority of the rays hit the wall of the clad rod, reflect from this hitting point to another point of the wall etc. The final result is that a beam of rays is obtained out of the end of the fibre optics 8 that faces the prism, the angular distribution of the ray beam being very even as such already. Accordingly, an even light cone is obtained from the output end of the fibre optics 8. It shall be noted that FIG. 2 shows, for the sake of clarity, the passage of a few rays only. A still better evenness may preferably be achieved by arranging a small diffusor 9 on the path of the ray beam coming from the output end of the clad rod 8. Ground glass, for instance, may be used as the diffusor 9. A lens or a lens combination 11 can be arranged between the clad rod 8 and the optical window 2, preferably between the diffusor 9 and the optical window 2, by means of which lens or lens combination a light cone is directed to the reflection surface of the optical window, i.e. to the surface which is in contact with the process solution.

FIG. 3 illustrates an example of an actual refractometer utilizing the solution according to the invention. FIG. 3 uses the same reference numerals as FIG. 1 and 2 for identical points. In FIG. 3 additionally, the reference numeral 10 indicates a light sensitive detector, by means of which the information of the location of the critical angle of total reflection, i.e. the borderline 7, is transformed into an electrical form.

The above example is by no means intended to restrict the invention, but the invention may be modified quite freely within the scope of the claims. So, it is clear that the refractometer according to the invention or its details do not necessarily have to be just like those shown in the figures, but solutions of another kind are also possible. For instance, the prism does not need to be absolutely quite similar to the prism of the figures, etc.

I claim:

1. A refractometer comprising a frame structure, in which are arranged a light source, a fibre optic clad rod of predetermined diameter, an optical window and a light sensitive detector, the optical window being positioned into contact with a solution having a concentration and a critical angle of total reflection related thereto to be measured and said light source producing a beam of rays directed to an interface between the optical window and the solution such that part of the ray beam reflects back from the solution and part of it is absorbed partially into the solution, an image being created in which a light area and an adjacent dark area define a borderline therebetween, said borderline having a location depending on the critical angle of total reflection, this angle being a function of the concentration of the solution, the light sensitive detector for detecting and converting into electrical form the location of the borderline, said fibre optic clad rod being arranged between the light source and the optical window, such that said ray beam passes through said rod to the optical window, and said clad rod being fitted to the light source for collecting a conical ray beam from the light source while removing wide angles of light rays and mixing and homogenizing the ray beam by internal reflection in the clad rod to create a beam of rays comprising a multiplicity of non-parallel rays at differing angles such that all angles of the ray beam have substantially equal amounts of light as said beam of rays exits said fibre optic clad rod.

2. A refractometer according to claim 1, wherein the diameter of the clad rod is essentially 1 to 2 mm.

3. A refractometer according to claim 2, wherein a lens or a lens combination is disposed between the clad rod and the optical window and directs the ray beam to the optical window.

4. A refractometer according to claim 2, comprising a diffusor which is disposed to diffuse the ray beam after the clad rod.

5. A refractometer according to claim 1, wherein a lens or a lens combination is disposed between the clad rod and the optical window and directs the ray beam to the optical window.

6. A refractometer according to claim 5, comprising a diffusor which is disposed to diffuse the ray beam after the clad rod.

7. A refractometer according to claim 1 comprising a diffusor which is disposed to diffuse the ray beam after the clad rod.

* * * * *

UNITED STATES PATENT AND TRADEMARK OFFICE
CERTIFICATE OF CORRECTION

PATENT NO. : 5,742,382
DATED      : April 21, 1998
INVENTOR(S): Jan KAHRE

It is certified that error appears in the above-indentified patent and that said Letters Patent is hereby corrected as shown below:

Title page,
At [73] Assignee, change "Janeksko Oy" to --Janesko Oy--.

Signed and Sealed this

Twenty-second Day of September, 1998

Attest:

BRUCE LEHMAN

Attesting Officer

Commissioner of Patents and Trademarks